United States Patent
Zou et al.

(10) Patent No.: US 7,112,724 B1
(45) Date of Patent: Sep. 26, 2006

(54) TRANSGENIC MANIPULATION OF SN-GLYCEROL-3-PHOSPHATE AND GLYCEROL PRODUCTION WITH A FEEDBACK DEFECTIVE GLYCEROL-3-PHOSPHATE DEHYDROGENESE GENE

(75) Inventors: Jitao Zou, Saskatoon (CA); Yangdou Wei, Saskatoon (CA); Cyril Periappuram, Ames, IA (US); Gopalan Selvaraj, Saskatoon (CA); Raju Datla, Saskatoon (CA)

(73) Assignee: National Research Council of Canada, Ottawa (CA)

( * ) Notice: Subject to any disclaimer, the term of this patent is extended or adjusted under 35 U.S.C. 154(b) by 459 days.

(21) Appl. No.: 10/088,079

(22) PCT Filed: Sep. 21, 2000

(86) PCT No.: PCT/CA00/01096

§ 371 (c)(1),
(2), (4) Date: Jul. 19, 2002

(87) PCT Pub. No.: WO01/21820

PCT Pub. Date: Mar. 29, 2001

Related U.S. Application Data (60) Provisional application No. 60/155,133, filed on Sep. 22, 1999.

(51) Int. Cl.
*A01H 5/00* (2006.01)
(52) U.S. Cl. .................. 800/298; 800/278; 800/281
(58) Field of Classification Search .............. 800/278, 800/281, 298
See application file for complete search history.

(56) References Cited

FOREIGN PATENT DOCUMENTS

| | | |
|---|---|---|
| CA | 2170611 | 9/1994 |
| EP | 0 843 007 | 5/1998 |
| WO | WO 92/13082 | 8/1992 |
| WO | WO 95/06733 | 3/1995 |
| WO | WO 96/38573 | 12/1996 |
| WO | WO 99/28480 | 6/1999 |
| WO | WO 03/095655 A2 | 11/2003 |

OTHER PUBLICATIONS

Clark, D. et al., *Regulation Of Phospholipid Biosynthesis in Escherichia-coli: Cloning Of The Structural Gene For The Biosynthetic sn-Glycerol-3-Phosphate Dehydrogenase EC-1.1.1.8*, Journal of Biological Chemistry, vol. 225, No. 2, 1980, pp. 714-717, XP002154728.

Edgar, J. R. et al., *Biosynthesis in Eschericia-coli Of SN Glycerol 3 Phosphate, A Precursor Of Phospho Lipid Purification And Physical Characterization Of Wild Type And Feedback Resistant Forms Of The Biosynthetic sn-Glycerol-3-Phosphate Dehydrogenase EC-1.1.1.8*, Journal Of Biological Chemistry, vol. 253, No. 18, 1978, pp. 6348-6353, XP002154729.

Gee, Robert et al., *Two Isoforms Of Dihydroxyacetone Phosphate Reductase From The Chloroplasts Of Dunaliella Tertiolecta*, Plant Physiology (Rockville), vol. 103, No. 1, 1993, pp. 243-249, XP002154757.

Hausmann, L. et al., *Cloning Of A cDNA Coding For A Glycerol-3-Phosphate Dehydrogenase From Cuphea Lanceolata*, Plant Lipid Metabolism,, 1995, pp. 534-536, XP000949817.

Larsson, K. et al., *A Gene Encoding SN-Glycerol 3-Phosphate Dehydrogenase (NAD+) Complements An Osmosensitive Mutant Of Saccharomyces Cerevisiae*, Molecular Microbiology, GB, Blackwell Scientific, Oxford, vol. 10, No. 5, 1993, pp. 1101-1111, XP000562759.

*Primary Examiner*—Elizabeth F. McElwain
(74) *Attorney, Agent, or Firm*—TraskBritt (57) ABSTRACT

The invention provides a method for genetically transforming a plant so that it expresses a glycerol-3-phosphate dehydrogenase that is feedback-defective. The feedback-defective enzyme raises levels of glycerol and glycerol-3-phosphate in comparison to the wild-type, leading to increased osmotic stress tolerance, and altered fatty acid content in glycerolipids.

14 Claims, 7 Drawing Sheets

Figure 1

```
  1 atgaaccaacgtaatgcttcaatgactgtgatcggtgccggctcg
    M  N  Q  R  N  A  S  M  T  V  I  G  A  G  S   15
 46 tacggcaccgctcttgccatcaccctggcaagaaatggccacgag
    Y  G  T  A  L  A  I  T  L  A  R  N  G  H  E   30
 91 gttgtcctctggggccatgaccctgaacatatcgcaacgcttgaa
    V  V  L  W  G  H  D  P  E  H  I  A  T  L  E   45
136 cgcgaccgctgtaacgccgcgtttctccccgatgtgccttttccc
    R  D  R  C  N  A  A  F  L  P  D  V  P  F  P   60
181 gatacgctccatcttgaaagcgatctcgccactgcgctggcagcc
    D  T  L  H  L  E  S  D  L  A  T  A  L  A  A   75
226 agccgtaatattctcgtcgtcgtacccagccatgtctttggtgaa
    S  R  N  I  L  V  V  V  P  S  H  V  F  G  E   90
271 gtgctgcgccagattaaaccactgatgcgtcctgatgcgcgtctg
    V  L  R  Q  I  K  P  L  M  R  P  D  A  R  L  105
316 gtgtgggcgaccaaagggctggaagcggaaaccggacgtctgtta
    V  W  A  T  K  G  L  E  A  E  T  G  R  L  L  120
361 caggacgtggcgcgtgaggccttaggcgatcaaattccgctggcg
    Q  D  V  A  R  E  A  L  G  D  Q  I  P  L  A  135
406 gttatctctggcccaacgtttgcgaaagaactggcggcaggttta
    V  I  S  G  P  T  F  A  K  E  L  A  A  G  L  150
451 ccgacagctatttcgctggcctcgaccgatcagaccttTgccgat
    P  T  A  I  S  L  A  S  T  D  Q  T  F  A  D  165
496 gatctccagcagctgctgcactgcggcaaaagtttccgcgtttac
    D  L  Q  Q  L  L  H  C  G  K  S  F  R  V  Y  180
541 agcaatccggatttcattggcgtgcagcttggcggcgcggtgaaa
    S  N  P  D  F  I  G  V  Q  L  G  G  A  V  K  195
586 aacgttattgccattggtgcggggatgtccgacggtatcggtttt
    N  V  I  A  I  G  A  G  M  S  D  G  I  G  F  210
631 ggtgcgaatgcgcgtacggcgctgatcacccgtgggctggctgaa
    G  A  N  A  R  T  A  L  I  T  R  G  L  A  E  225
676 atgtcgcgtcttggtgcggcgctgggtgccgaccctgccacctTt
    M  S  R  L  G  A  A  L  G  A  D  P  A  T  F  240
721 atgggcatggcggggcttggcgatctggtgcttacctgtaccgaa*
    M  G  M  A  G  L  G  D  L  V  L  T  C  T  E  255
766 aaccagtcgcgtaaccgccgttttggcatgatgctcggtcagggc
    N  Q  S  R  N  R  R  F  G  M  M  L  G  Q  G  270
811 atggatgtacaaagcgcgcaggagaagattggtcaggtggtggaa
    M  D  V  Q  S  A  Q  E  K  I  G  Q  V  V  E  285
856 ggctaccgcaatacgaaagaagtccgcgaactggcgcatcgcttc
    G  Y  R  N  T  K  E  V  R  E  L  A  H  R  F  300
901 ggcgttgaaatgccaataaccgaggaaatttatcaagtattatat
    G  V  E  M  P  I  T  E  E  I  Y  Q  V  L  Y  315
946 tgcggaaaaaacgcgcgcgaggcagcattgactttactaggtcgt
    C  G  K  N  A  R  E  A  A  L  T  L  L  G  R  330
991 gcacgcaaggacgagcgcagcagccactaa                 1020
    A  R  K  D  E  R  S  S  H  *                   339
```

TRANSGENIC MANIPULATION OF SN-GLYCEROL-3-PHOSPHATE AND GLYCEROL PRODUCTION WITH A FEEDBACK DEFECTIVE GLYCEROL-3-PHOSPHATE DEHYDROGENESE GENE

CROSS-REFERENCE TO RELATED APPLICATION

This application claims the priority right of provisional application Ser. No. 60/155,133 filed Sep. 22, 1999 by applicants herein.

FIELD OF THE INVENTION

The invention relates to the field of plant genetic engineering. More specifically, the invention relates to methods for manipulating the glycerol-3-phosphate metabolism of a plant by expressing in the plant a gene for a feedback-defective glycerol-3-phosphate dehydrogenase.

BACKGROUND OF THE INVENTION

Glycerol-3-phosphate dehydrogenase (GPDH) (EC 1.1.1.8) is an essential enzyme for both prokaryotic and eukaryotic organisms. It catalyzes the reduction of dihydroxyacetone phosphate (DHAP) to glycerol-3-phosphate (G-3-P) using NADH as reducing equivalent. Plant cells possess at least two isoforms of GPDH, one located in the plastids and the other in the cytosol.[1] The purification of the cytosolic GPDH from spinach has been reported. The product of the reaction catalyzed by GPDH, G-3-P, is a precursor for the synthesis of all glycerol lipid species, including membrane and storage lipids. The biosynthetic role of this enzyme in bacteria was established in vivo by the isolation of glycerol and G-3-P auxotrophs of *E. coli* mutant strains deficient in its activity.[3] These mutants could not synthesize phospholipid in the absence of supplemental G-3-P.

There are no reports of plant mutants defective in GPDH activity.

In addition to being essential for lipid biosynthesis, GPDH is involved in several other important biological processes. Most notably, GPDH, through consuming NADH and regenerating NAD$^+$, plays an important role in maintaining cellular redox status. The NAD$^+$/NADH couple plays a vital role as a reservoir and carrier of reducing equivalents in cellular redox reactions. For catabolic reactions to proceed, the ratio NAD$^+$/NADH should be high. Under normal aerobic conditions, excessive NADH is channeled into mitochondria and consumed through respiration. Under anaerobic conditions, GPDH reactions serve as a redox valve to dispose of extra reducing power. In this way, the cellular NAD+/NADH ratio can be maintained at a level allowing catabolic processes to proceed. The expression of the GPDH gene is subject to redox control and induced by anoxic conditions in *Saccaromyces cerevisae*. Deletion of the GPD2 gene (one of the two isoforms of GPDH) results in defective growth under anaerobic conditions.[4]

GPDH has also been shown to play an important role in adaptation to osmotic stress in *Saccaromyces cerevisae*. GPDH exerts its role in osmotic and salinity stress response through its function in glycerol synthesis. Glycerol is a known osmo-protectant. It is produced from G-3-P through dephosphorylation by a specific glycerol 3-phosphatase. To respond to a high external osmotic environment, yeast cells accumulate glycerol to compensate for differences between extracellular and intracellular water potentials.[5] The expression of the GPDH gene, GPD1, has been demonstrated to be osmo-responsive.[6] A strain of *Saccaromyces* cerevisae in which the GPD1 gene has been deleted is hypersensitive to NaCl.[7] Accumulation of glycerol as an osmo-regulatory solute has been reported in some halophilic green algae including *Dunaliella, Zooxanthellae, Asteromonas* and *Chlamydonas reinhardtii*.[8]

The sequence of a cDNA encoding GPDH activity has been reported for the plant *Cuphea lanceolata*.[9] The encoded protein was tentatively assigned as a cytosolic isoform.

To date, there has been no report on the genetic manipulation of plant GPDH.

SUMMARY OF THE INVENTION

It is an object of the invention to provide a method for expressing in a plant a heterologous glycerol-3-phosphate dehydrogenase.

It is an object of the invention to provide a plant expressing a heterologous glycerol-3-phosphate dehydrogenase, wherein the heterologous glycerol-3-phosphate dehydrogenase is subject to less feedback inhibition than wild-type glycerol-3-phosphate dehydrogenase.

It is a further object of the invention to provide a genetically altered plant exhibiting altered fatty acid content in its glycerolipids.

It is a further object of the invention to provide a genetically altered plant exhibiting enhanced tolerance to osmotic stress in comparison to the wild-type plant.

It is a further object of the invention to provide a genetically altered plant exhibiting increased stress tolerance in comparison to the wild-type plant.

In a first aspect, the invention provides a method for expressing in a plant a heterologous glycerol-3-phosphate dehydrogenase that is less sensitive to feedback inhibition than wild-type glycerol-3-phosphate dehydrogenase, the method comprising the steps of:
  providing a vector comprising a DNA sequence encoding a glycerol-3-phosphate dehydrogenase that is less sensitive to feedback inhibition than wild-type glycerol-3-phosphate dehydrogenase; and
  transforming the plant with the vector.

In a second aspect, the invention provides a plant expressing a heterologous glycerol-3-phosphate dehydrogenase that is less sensitive to feedback inhibition than wild-type glycerol-3-phosphate dehydrogenase.

In a third aspect, the invention provides a method for producing a genetically altered plant having altered fatty acid content in its glycerolipids, the method comprising the steps of:
  providing a vector comprising a DNA sequence encoding a glycerol-3-phosphate dehydrogenase that is less sensitive to feedback inhibition than wild-type glycerol-3-phosphate dehydrogenase; and
  transforming the plant with the vector.

In a fourth aspect, the invention provides a method for producing a plant having increased glycerol and/or glycerol-3-phosphate levels, the method comprising the steps of:
  providing a vector comprising a DNA sequence encoding a glycerol-3-phosphate dehydrogenase that is less sensitive to feedback inhibition than wild-type glycerol-3-phosphate dehydrogenase; and
  transforming the plant with the vector.

In a fifth aspect, the invention provides a method for producing a genetically altered plant having increased stress tolerance relative to the wild-type, the method comprising the steps of:

providing a vector comprising a DNA sequence encoding a glycerol-3-phosphate dehydrogenase that is less sensitive to feedback inhibition than wild-type glycerol-3-phosphate dehydrogenase; and transforming the plant with the vector.

In a sixth aspect, the invention provides a method for producing a genetically altered plant having increased osmotic stress tolerance relative to the wild-type, the method comprising the steps of:

providing a vector comprising a DNA sequence encoding a glycerol-3-phosphate dehydrogenase that is less sensitive to feedback inhibition than wild-type glycerol-3-phosphate dehydrogenase; and transforming the plant with the vector.

In a seventh aspect, the invention provides a method for increasing the cellular glycerol-3-phosphate dehydrogenase activity in a plant, the method comprising the steps of:

providing a vector comprising a DNA sequence encoding a glycerol-3-phosphate dehydrogenase that is less sensitive to feedback inhibition than wild-type glycerol-3-phosphate dehydrogenase; and transforming the plant with the vector.

In an eighth aspect, the invention provides a vector for genetically transforming a plant, wherein the vector comprises a DNA encoding a protein having glycerol-3-phosphate dehydrogenase activity, and the plant, after transforming, exhibits enhanced production of glycerol and/or glycerol-3-phosphate.

BRIEF DESCRIPTION OF THE DRAWINGS

The invention is illustrated with the aid of the drawings, wherein:

FIG. 1 shows the nucleotide sequence and the deduced amino acid sequence of the *Escherichia coli* gpsA2$^{FR}$ gene. The point mutation is highlighted and denoted by "*";

DETAILED DESCRIPTION OF THE INVENTION

Due to its role in lipid biosynthesis as well as in the stress responses, an increased GPDH activity in plants is desirable. Transgenic approaches to over express either a plant or a non-plant GPDH gene in a plant can, in principle, be expected to increase GPDH activity. However, there are several advantages inherent in inserting a non-plant gene into a plant genome. It is well established that introducing the same plant gene back to its originating species, even under sense-orientation, can result in a decrease of the overall enzyme activity due to co-suppression. Genes of different origin (heterologous), especially those from evolutionarily-distant related species, can be expected to be free of this impediment. More importantly, proteins of identical enzymatic function are often regulated through different schemes in different species. A heterologous enzyme may potentially be free of controlling factors that inhibit the endogenous enzyme.

The heterologous enzyme that is expressed in the plant, in the method of the invention, may be any glycerol-3-phosphate dehydrogenase that exhibits decreased inhibition of glycerol-3-phosphate production in the plant. Such enzymes are called feedback-defective. In a preferred embodiment, the heterologous enzyme is a glycerol-3-phosphate dehydrogenase having a single amino acid mutation. The mutation should not greatly decrease glycerol-3-phosphate dehydrogenase activity, but should decrease inhibition of the enzyme by glycerol-3-phosphate. One allele of the *E. coli* gpsA gene, gpsA2$^{FR}$, has been reported to encode an altered version of the GPDH protein defective in feedback inhibition.[10] In a preferred embodiment, the method of the invention uses a vector comprising the gene gpsA2$^{FR}$. The inventors identified a point mutation in the gspA2$^{FR}$ sequence: replacement of A by C in the third nucleotide of codon 255 in gpsA. The mutation results in substitution of Glu$^{255}$ (GAA) for Asp$^{255}$ (GAC) in the encoded protein. The sequences of the gpsA2$^{FR}$ gene and the deduced amino acid sequence of the gene are shown in FIG. 1. The gene sequence is listed in SEQ ID NO: 1, and the encoded protein is listed in SEQ ID NO:2.

The vector may be any vector that is suitable for transforming the plant species used. Examples of suitable vectors include pHS737, pHS738, pRD400[11]; pBin19[12]; and pCGN3223.[13]

GPDH is common to the biosynthetic pathway of all plants. The method of the invention can therefore be used with any plant. The inventors chose to use the model plant species *Arabidopsis thaliana*. As a result of the ease with which this plant lends itself to work in both classical and molecular genetics, *Arabidopsis* has come to be widely used as a model organism in plant molecular genetics, development, physiology and biochemistry.[14, 15, 16] This dicotyledonous plant is also closely related to *Brassica* crop genus and it is increasingly apparent that information concerning the genetic control of basic biological processes in *Arabidopsis* will be transferable to other species.[17]

Indeed, there are numerous examples wherein studies of the molecular biology and biochemistry of a particular metabolic pathway or developmental process and the possibility of genetically engineering a plant to bring about changes to the metabolic pathway or process, has first been tested in the model plant *Arabidopsis*, and then shown to yield similar phenotypes in other plants, particularly crop plants.

Expressing a heterologous GPDH in a plant, according to the method of the invention, leads to altered fatty acid content in the triacylglycerols of the plant. It is often desirable to alter the fatty acid content of glycerolipids to achieve certain desired characteristics in oil seeds. For example, for oils destined for human consumption, it may be wished to increase unsaturated fatty acid content. For other uses, it may be desirable to increase the saturated fatty acid content. The inventors have found that plant transformants over-expressing the gpsA2$^{FR}$ gene produce glycerolipids having an increased proportion of 16 carbon fatty acids and a concomitant decrease of 18 carbon fatty acids.

Due to the relationship of GPDH to glycerolipid synthesis, the method of the invention is particularly suited for use with oil seed-bearing plants. The term "oil seed-bearing plant" is meant to encompass any plant or crop from which the oil may be isolated in marketable quantity. Some plants or crops having glycerolipids with particularly interesting fatty acid composition are grown for the production of glycerolipids, even though the lipid content is low (e.g., less than 1 wt %). The method of the invention may be used in such plants to modify the fatty acid content of the glycerolipid. Preferred plants or crops are those having a seed lipid content of at least 1 wt %. Some illustrative examples of oil seed crops are as follows (trivial names are given in parentheses):

*Borago officinalis* (Borage); *Brassica* species, for example mustards, canola, rape, *B. campestris, B. napus, B. rapa; Cannabis sativa* (Hemp, widely used as a vegetable oil in Asia); *Carthamus tinctorius* (Safflower); *Cocos nucifera* (Coconut); *Crambe abyssinica* (Crambe); *Cuphea* species (*Cuphea* produce medium chain fatty acids of industrial interest); *Elaeis guinensis* (African oil palm); *Elaeis oleifera* (American oil palm); *Glycine max* (Soybean); *Gossypium hiristum* (Cotton—American); *Gossypium barbadense* (Cotton—Egyptian); *Gossypium herbaceum* (Cotton—Asiatic); *Helianthus annus* (Sunflower); *Linum usitatissimum* (Linseed or flax); *Oenethera biennis* (Evening primrose); *Olea europea* (Olive); *Oryza sativa* (Rice); *Ricinus communis* (Castor); *Sesamum indicum* (Sesame); *Soja max* (Soybean—note *Glycine max* is the major species); *Triticum* species (Wheat); and *Zea maize* (Corn).

GPDH consumes NADH, and therefore plays an important role in maintaining a healthy cellular redox balance. Stress conditions often result in perturbation of plant metabolism, and particularly redox status. Stress conditions include such things as dryness, excessive humidity, excessive heat, excessive cold, excessive sunlight, and physical damage to the plant. Such agents can lead to higher than normal levels of NADH. Excessive NADH can generate high concentrations of reactive oxygen species (ROS) that are hazardous to proteins and nucleic acids, and may even lead to cell death. An increased GPDH activity, as induced by the method of the invention, improves the capacity of plants to maintain cellular redox balance, thereby leading to an enhanced tolerance to stress.

Another type of stress suffered by plants is osmotic stress. This results when the plant is forced to grow in an environment in which the external water supply has an unusually high concentration of solute. The most usual solutes that are encountered include salts (particularly NaCl), however, in polluted areas, other solutes might be encountered. The method of the invention leads to increased levels of glycerol and/or gycerol-3-phosphate in the tissues of the transformed plant. Glycerol acts as an osmo-protectant, allowing the transformed plant to grow in conditions that would normally not support it.

A heterologous gene encoding GPDH activity can be introduced into the genome of plants and expressed using conventional genetic engineering techniques. The most developed methodology for inserting genes into plant genomes is *Agrobacterium tumefaciens* mediated transformation. Other techniques known in the art of introducing DNA into plants include electroporation, chemically-mediated DNA uptake, and the use of microprojectiles.

The invention will be described in more detail with reference to the following examples. The examples serve only to illustrate the invention.

Specific Embodiments a. Molecular Biological Techniques

For a general description of some of the techniques used, see Ausebel et al *Current protocols in Molecular Biology*, Vols. 1, 2, 3, (1995) New York: Wiley, incorporated herein by reference.

b. Identification of the Point Mutation of the gpsA2$^{FR}$ gene from *Escherichia coli* Strain BB26R.

In order to investigate the structure of the gpsA2$^{FR}$ gene, the inventors synthesized two primers, TTAGTGGCTGCT-GCGCTC (GPSA3, SEQ ID NO:3) and AACAATGAAC-CAACGTAA (GPSA5, SEQ ID NO:4), complementary to the sequences corresponding to the 3' and 5' end of the gpsA gene, respectively. PCR amplifications were performed with template DNA isolated from wild-type *E. coli* K12 and from strain BB26R, respectively. The BB26R strain harboring the gpsA2$^{FR}$ allele can be obtained according to Cronan et al. The PCR products were purified with QIAquick™ PCR purification Kit (Qiagen™) and fully sequenced. The sequences of gpsA (wild-type) and gpsA2$^{FR}$ (mutant) were compared through sequence alignment using the computer program DNAstar™.

c. Construction of a Plant Transformation Vector for gpsA$^{FR}$

Primers GAGAGCTCTTAGTGGCTGCTGCGCTC (GPSA31, SEQ ID NO:5) and GAAGAAGGATCCAA-CAATGAACCAACGTAA (GPSA51, SEQ ID NO:6) were designed according to the sequence of gpsA2$^{FR}$. At the 5' end of GPSA31, a SacI restriction site was added, while a BamHI restriction site was added at the 5' end of GPSA5. The primers were used to perform PCR amplification of the gpsA2$^{FR}$ sequence. The PCR products were purified with QIAquick™ PCR purification Kit (Qiagen) and digested with SacI/BamHI. The SacI/BamHI digested gpsA2$^{FR}$ DNA fragment was subsequently inserted into the *Agrobacterium* binary vector pBI121 (Clontech) to replace the SacI/BamHI region covering the GUS gene. The resultant plant transformation vector is designated as pGPSA-VI (deposited Aug. 31, 2000, at the American Type Culture Collection, 10801 University Blvd. Manassa, Va. 20110-2209, accession no. PTA-2433). The gpsA2$^{FR}$ gene expression cassette in pGPSA-VI contains the gpsA2$^{FR}$-encoding region driven by the constitutive 35S promoter. Its 3' end is flanked by the NOS terminator. The junction region between the 35S promoter and the gpsA2$^{FR}$ encoding sequence in pGPSA-VI was confirmed through sequencing. The gpsA2$^{FR}$ protein will thus be expressed in all plant tissues including vegetative and reproductive (seed) tissues once the gene expression cassette is incorporated into the plant genome.

d. Plant Growth Conditions

*Arabidopsis thaliana* was chosen as the plant host to test the effect of the gpsA2$^{FR}$ gene since it is widely recognized as a laboratory model plant for genetic and biochemical studies. Moreover, *A. thaliana* in many aspects resembles *Brassica napus*, and is considered an oil seed plant. Genetic manipulations that are successful with *A. thaliana* can be applied to other species.[18] All *A. thaliana* control and transgenic plants were grown at the same time, in controlled growth chambers, under 16 hours fluorescent illumination (150–200 µE.m$^{-2}$.sec$^{-1}$), 8 hours dark at 22° C., as described previously.[19]

e. Plant Transformation

Plasmid pGPSA-VI was introduced into *Agrobacterium tumefaciens* strain GV3101 bearing helper nopaline plasmid pMP90, via electroporation. Wild-type *A. thaliana* plants of ecotype Columbia were grown in soil. Plants one week after bolting were vacuum-infiltrated over night with a suspension of *A. tumefaciens* strain GV3101 harboring pGPSA-VI.[20]

After infiltration, plants were grown to set seeds (T1). Dry seeds (T1) were harvested in bulk and screened on selective medium with 50 mg/L kanamycin. After two to three weeks on selective medium, kanamycin-resistant seedlings (T1) which appeared as green were transformed to soil to allow growing to maturity. Seeds (T2) from the T1 plants were harvested and germinated on kanamycin plates to test segregation ratios. A typical single gene insertion event would give rise to a kanamycin-resistant/sensitive ratio of 3:1. To further confirm the integration of the $gpsA2^{FR}$ gene, DNA was isolated from selected transgenic lines to perform Southern blot analysis with probes prepared with $gpsA2^{FR}$ DNA. Total RNA was also isolated for Northern analysis to confirm the expression of the $gpsA2^{FR}$ gene.

f. Fatty Acid Profile Analysis

Lipids were isolated from developing leaves as described by Katavic et al.[21] and the fatty acid compositions were analyzed by Gas Chromatography.

g. Analysis of Plant Tolerance Towards Salinity Stress

The salt tolerance of *A. thaliana* ecotype Columbia (wild-type) plants and plants over-expressing the $gpsA2^{FR}$ gene was measured using a protocol reported by Apse et al.[22] Pots of wild-type plants and each of the four transgenic lines (designated as #7, #13, #54 and #58) over-expressing $gpsA2^{FR}$ gene were divided into five groups (labeled A through E). The plants were planted in 4-inch pots with each pot containing 4 plants. The plants were grown for two weeks with nutrients-only (22 g of 20:20:20 plant nutrient (Plant Products Co. Ltd., Canada) in 80 liters of water) solutions to ensure even growth of all plants. Afterwards, every alternate day over a 16-day watering regime, 25 ml of a diluted nutrient solution was applied. The control (A) group received the nutrient-only solution with no NaCl supplementation. The remaining groups were watered with nutrient solution supplemented with NaCl. The concentrations of NaCl supplementation were increased stepwise by 50 mM every 4 days for each group, to the indicated maximum: (A) 0 mM NaCl, (B) 50 mM NaCl, (C) 100 mM NaCl, (D) 150 mM NaCl, and (E) 200 mM NaCl. The plants were monitored for their phenotype, flowering time, etc.

Seed germination assays were performed with surface-sterilized *Arabidopsis* seeds of wild-type and selected T3 transgenic lines sown in Petri dishes containing 20 ml half strength MS medium,[23] supplemented with B5 vitamins and 2% sucrose. For the salt stress germination assay, various concentrations of NaCl were added. Cultures were grown at 22° C. under fluorescent light, 16 hours light and 8 hours dark. Seed germination was recorded after a period of 10 days. The emergence of radicle and cotyledons was considered as evidence of germination.

Results

The $gpsA2^{FR}$ Gene has a Point Mutation that Alters One Amino Acid Residue in the GPDH Protein ($gpsA2^{FR}$)

The biosynthesis of G-3-P in *Escherichia coli* was initially investigated by Kito and Pizer.[24] The gpsA locus located at minute 71 of the *E. coli* genetic map was determined to be the structural gene for the biosynthetic glycerol-3-phosphate dehydrogenase by Cronan and Bell.[25] The nucleotide sequence and the deduced amino acid sequence of the *Escherichia coli* gpsA gene was reported previously.[26] Biochemical studies on phospholipid biosynthesis mutants indicated that the cellular level of G-3-P must be tightly regulated Bell (1974), *J. Bacteriol.* 117, 1065–1076]. The *E. coli* mutant, plsB, possesses a glycerol-P acyltransferase with an apparent $K_m$ for G-3-P over 10 times higher than normal. Subsequently, revertants of the plsB mutant, BB26R, were identified.[27] The glycerol-3-phosphate dehydrogenase activities of these revertants were about 20-fold less sensitive to feedback inhibition by G-3-P. These feedback-resistant gpsA alleles were named $gpsA2^{FR}$. The molecular mechanism behind the $gpsA2^{FR}$ protein was unknown. The $gpsA2^{FR}$ cloned gene was from strain BB26R and its nucleotide sequence was determined. Sequence analysis indicated that $gpsA2^{FR}$ differs from gpsA at only one nucleotide base. The point mutation, a replacement of A from C at the third nucleotide of codon 255 in gpsA (FIG. 1) was founded in the $gpsA2^{FR}$ gene. This point mutation resulted in a change of $Glu^{255}$ (GAA) from $Asp^{255}$ (GAC) in the glycerol-3-phosphate dehydrogenase enzyme protein.

It has now been shown that the $gpsA2^{FR}$ gene harbors a point mutation in comparison to the wild-type gpsA gene. The inventors have demonstrated that the point mutation is the reason why the GPDH enzyme is 20 times less sensitive to G-3-P feedback inhibition than the wild-type. As a result, the cellular G-3-P could reach a level higher than a wild-type gpsA could generate.

Figure 2:
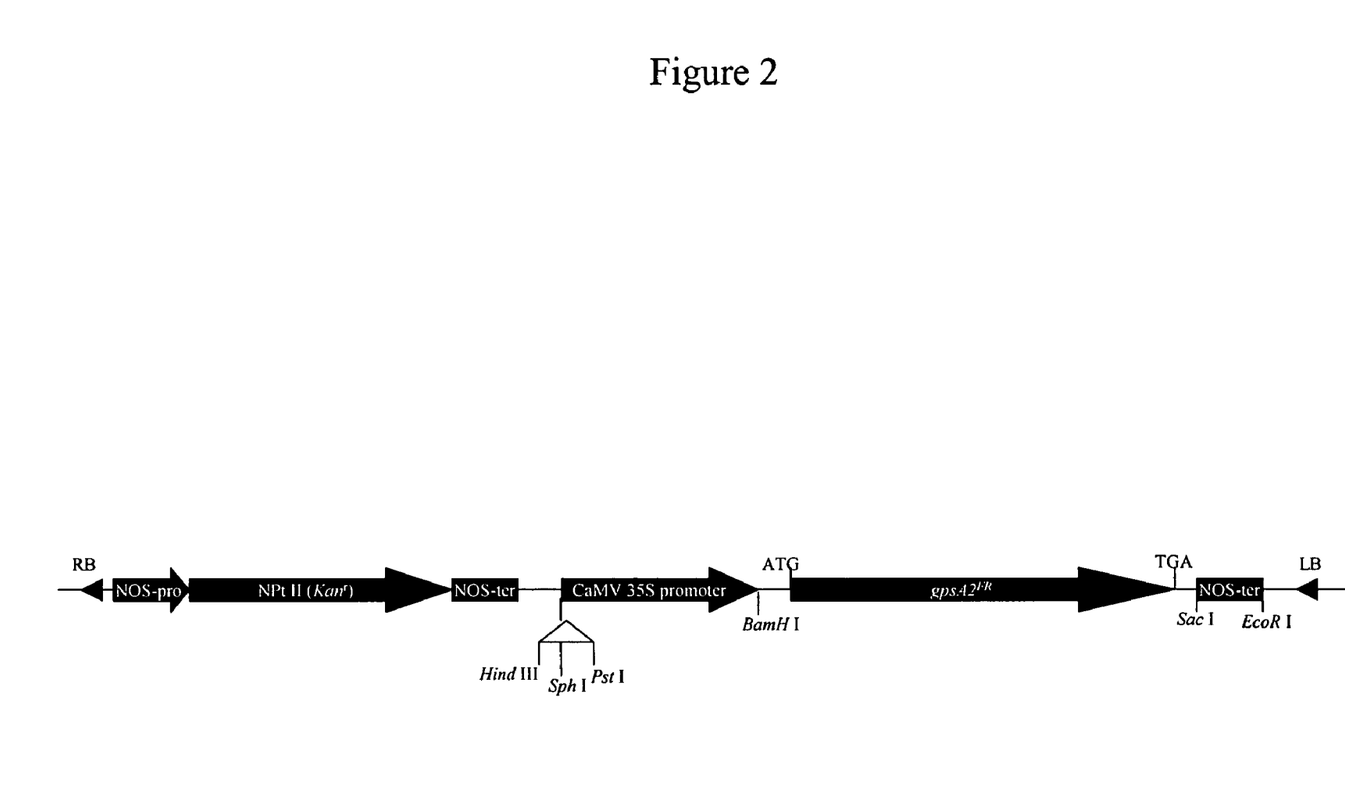
FIG. 2 shows a diagram of the gpsA2$^{FR}$ plant transformation vector, pGPSA-VI, not drawn to scale.
Figure 3:
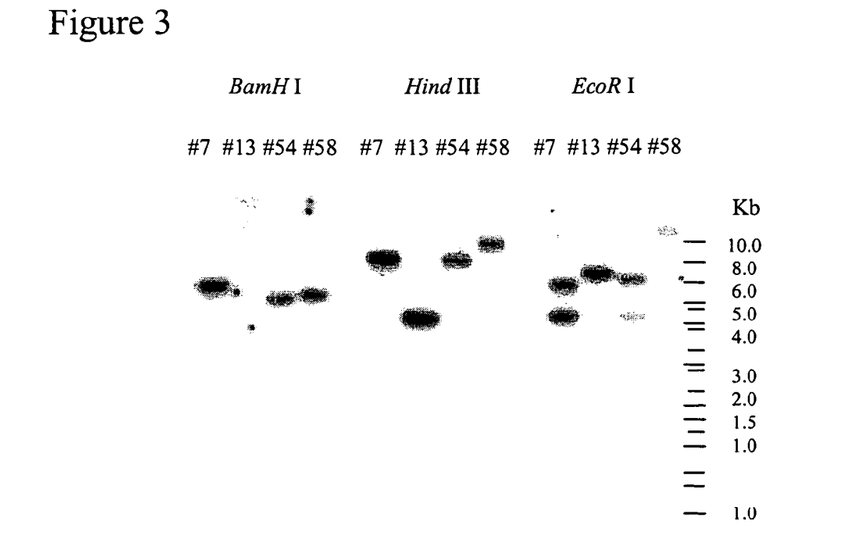
FIG. 3 shows a southern blot analysis with respect to the gpsA2$^{FR}$ gene among the selected independent *Arabidopsis thaliana* transgenic lines.
Figure 4:
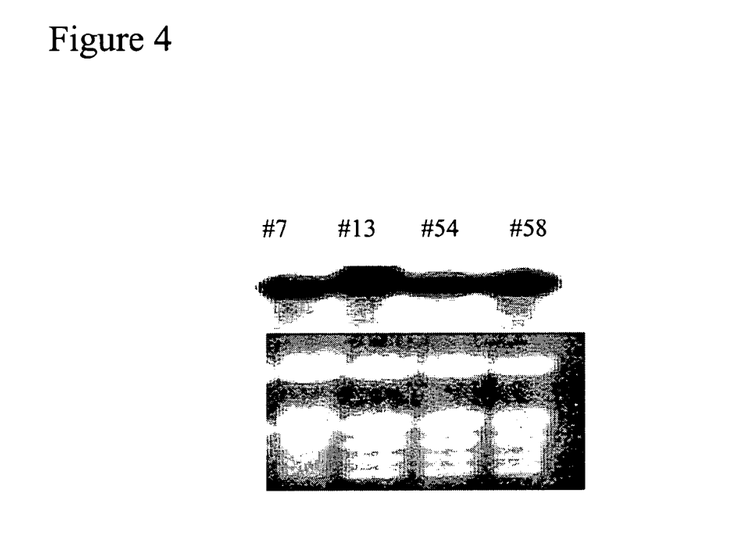
FIG. 4 shows a northern blot analysis of gpsA2$^{FR}$ gene expression in the *A. thaliana* transgenic lines.

Introduction of the $gpsA2^{FR}$ Gene into Plant Genomes does not Affect Plant Development A large number of $gpsA2^{FR}$ transgenic plants were generated. These transgenic plants (T1) were initially screened for kanamycin resistance in kanamycin supplemented ½ MS medium. All T1 transgenic plants under our growing conditions appeared indistinguishable from wild-type *A. thaliana* control, and developed at the same pace as that of the wild-type plants when transferred into soil. The fertility and the seed yield were also not affected by the transgene. It thus proved that the integration of the $gpsA2^{FR}$ gene did not have any adversary effect on plant growth and reproduction. The segregation ratios of the (T2) seeds from the T1 plants with regard to kanamycin resistance were investigated. Transgenic lines #7, #13, #54, #58 were selected for further study since segregation analysis indicated that these lines were single-insertion transgenic lines. To further verify the incorporation of $gpsA^{FR}$ gene into plant genome, genomic DNA was isolated from T3 plant seedlings of lines #7, #13, #54, #58, respectively. Southern analysis of genomic DNA digested with three different restriction enzymes showed that these lines contain a single copy of the $gpsA2^{FR}$ gene, and the transgene is inherently stable (FIG. 4). Northern analysis with RNA extracted from these lines confirmed that the $gpsA2^{FR}$ gene is expressed at a high level in these transgenic lines. Therefore, the introduction and expression of the $gpsA2^{FR}$ gene into higher plants was accomplished.

*A. thaliana* $gpsA2^{FR}$ Transformants Have Altered Fatty Acid Profiles

Figure 5:
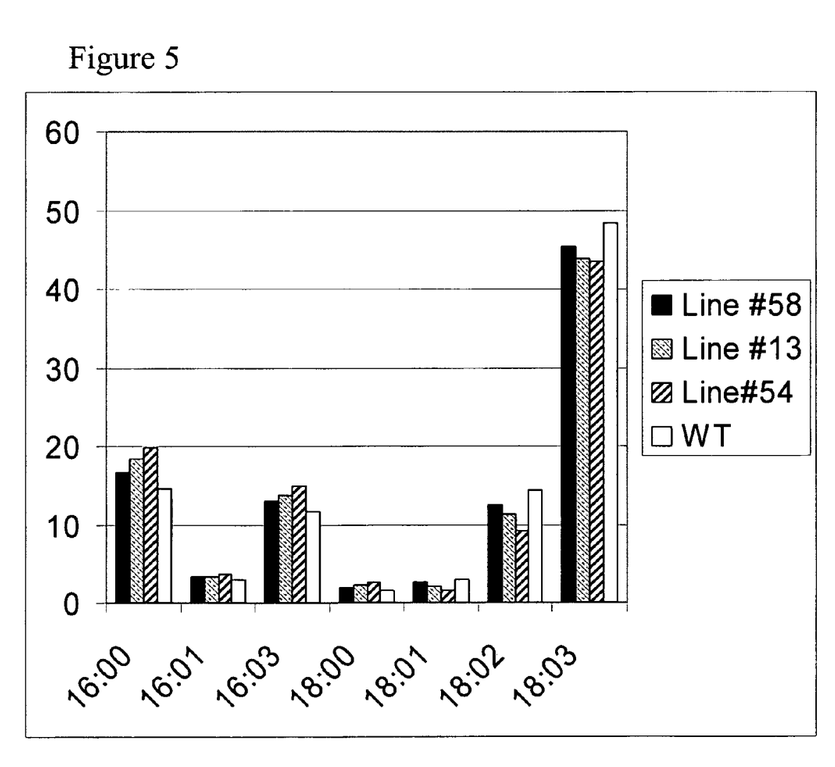
FIG. 5 shows the leaf fatty acid profiles of the selected gpsA2$^{FR}$ transgenic *Arabidopsis thaliana* lines.

Total lipids were extracted from leaf tissues of transgenic plants as well as wild-type control, and the fatty acid compositions were analyzed using Gas Chromatography. In order to minimize any difference that might exist during plant development, care was taken to ensure all plant leaves collected were at the same developmental stage. Reproducible results were obtained with leaves collected from several wild-type plants, confirming that there were no significant differences with regard to fatty acid profiles among wild-type plants. Data from leaves of the *A. thaliana* transgenic plants, however, indicated that the gpsA2$^{FR}$ gene product affects fatty acid composition. As shown in FIG. 5, gpsA2$^{FR}$ transgenic plants consistently had elevated levels of 16 carbon fatty acids, and a proportionately decreased level of 18 carbon fatty acids. Specifically, the transgenic plants showed about a 2–5% increase of 16:0, and about a 1.5–3.5% increase of 16:3 fatty acids. Concomitantly, the decrease on 18:2 and 18:3 fatty acids is at a 2–5% range (FIG. 5). Differences between the transgenic plants and the controls are also apparent if the ratios of the sum of 16-carbon (16C) fatty acid versus the sum of 18-carbon (18C) fatty acids are compared. For example, under the growing conditions described, transgenic line #58, line #13 and line #54 had 16C/18C ratios of 0.53, 0.6 and 0.68, respectively, while the ratio in control plants was 0.43. This phenotype is most likely a direct result of an increased supply of G-3-P generated by the high GPDH activity in the transgenic plants. It is consistent with a previous report by Gardiner et al, in which an increased ratio of 16C/18C fatty acids was observed among newly synthesized fatty acids when elevated amounts of G-3-P were fed to isolated plastids.[28]

The gpsA2$^{FR}$ Gene Improved Plant Stress Tolerance

As stated previously, GPDH consumes NADH and regenerates NAD$^+$. Lowering cellular [NADH] has beneficial effects on mitochondrial respiration and energy charge. GPDH participates in the control of cellular redox status, and possibly reduces the concentration of potentially damaging reactive oxygen species. Plant cells are known to go through an oxidative burst under stress conditions, often leading to cell death.

The present study revealed that the gpsA2$^{FR}$ transgenic plants possessed enhanced salinity tolerance.

Figure 6:
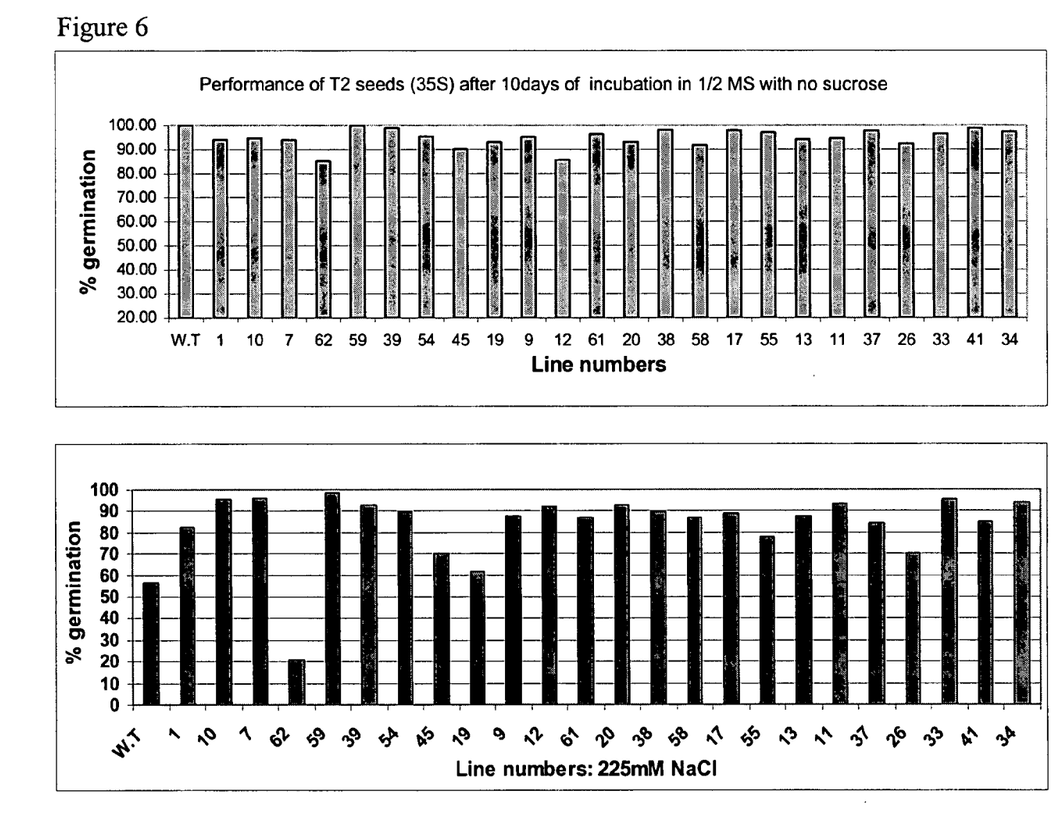
FIG. 6 shows the germination rate of the seeds produced by the selected *Arabidopsis thaliana* transgenic lines in ½ MS medium with or without 225 mM NaCl.
Figure 7:
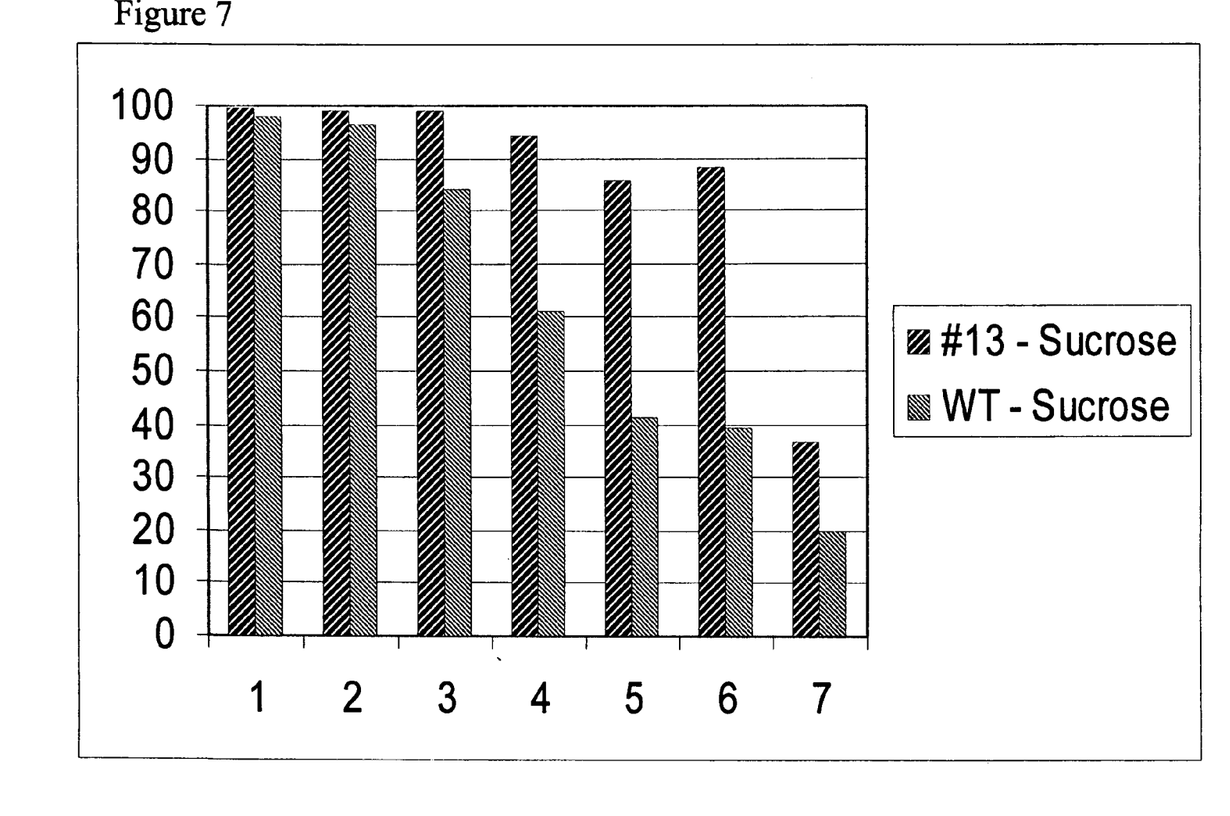
FIG. 7 shows the germination rate of wild-type *A. thaliana* and transgenic line #13 seeds in ½ MS media supplemented with various concentrations of NaCl.

The enhanced salinity tolerance could be observed at different developmental stages. Transgenic plant seeds germinated at the same frequency as that of the non-transgenic control plants on ½ MS medium (FIG. 6, upper panel). However, on media with added salt (FIG. 6, lower panel), the wild-type germinated at only about 55%, while transgenic lines #54, #58, #7 and #13 germinated at a rate of 90%, 86%, 87% and 95%, respectively. The germination frequencies of line #13 seeds were further evaluated with various NaCl concentrations. As shown in FIG. 7, in all concentrations of NaCl examined, line #13 seeds consistently showed higher germination rates than that of the wild-type plant seeds. The most dramatic effect was observed with 250 mM NaCl, in which less than 40% of wild-type seeds germinated, while 80% of the line #13 seeds germinated. In neither cases could auxotrophic growth be established from the germinated seeds.

Figure 8:
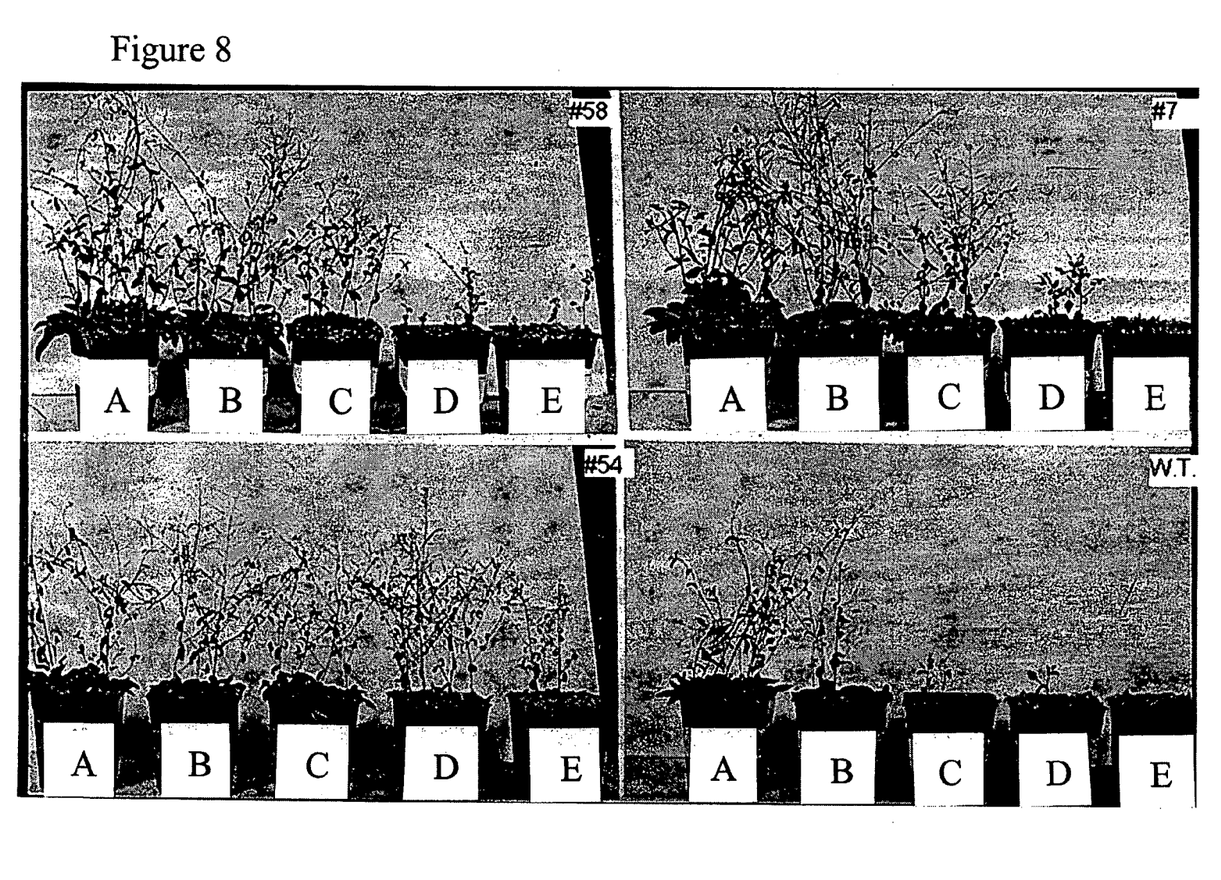
FIG. 8 shows the performance of the soil-grow transgenic plants under various degrees of salinity stress as detailed in Experimental Details.

Wild-type *A. thaliana* could germinate reasonably well (80%) on medium containing 175 mM NaCl. However, seedling growth and development were severely retarded. In contrast, the growth rate of the transgenic plants was substantially higher. After 6 weeks, wild-type plants developed chlorosis on leaf tissues and eventually died, while under the same conditions the transgenic plants still maintain relatively healthy green leaves. Plants growing in soil were also investigated with respect to salinity tolerance. The inventors followed the treatment protocol reported by Apse et al.,[29] designed to mimic field stress conditions. As shown in FIG. 8, the transgenic plants displayed advanced growth and developmental profiles in comparison to those of wild-type plants. Most of the wild-type plants repeatedly treated with 50 mM NaCl appeared severely stressed with darkened leaf color. The same treatment did not seem to affect the growth and reproduction of the transgenic lines. Wild-type plants ceased to grow and eventually died when solutions containing salt at 100 mM were applied, while the majority of the transgenic plants developed to maturity and produced seeds. When a watering regime was carried out to a salt concentration of 150 mM NaCl, the transgenic plants showed apparent stressed phenotype, but were still able to produce seeds, albeit with short siliques and very little seed yield. Plants from line # 54 exhibited the most improved salinity among the transgenic lines tested. They produced seeds even when watering reached a salt concentration of 200 mM NaCl.

REFERENCES (INCORPORATED HEREIN BY REFERENCE)

1 Gee et al., (1988) *Plant Physiol.* 86, 98–103; Gee et al., (1988) *Plant Physiol.* 87, 379–383.
2 Kirsh et al, (1992) *Plant Physiol.* 100, 352–359.
3 Hsu and Fox (1970) *J. Bacteriol.* 103, 410–416; Bell (1974) *J. Bacteriol.* 117, 1065–1076.
4 Ansell et al., (1997), *EMBO J.* 16, 2179–2187.
5 Brown (1990), in *Micorbial Water Stress Physiology, Principles and Perspectives*. John Wiley & Sons, New York.
6 Larsson et al., (1993), *Mol Microbiol.* 10, 1101–1111.
7 Ansell et al., (1997), *EMBO J.* 16, 2179–2187.
8 Husic and Tolbert, (1986), *Plant Physiol.* 82, 594–596; Ben-Amotz and Avron, (1983), *Annu Rev Microbiol.* 37, 95–119.
9 Hausmann et al, (1995). In *Plant Lipid Metabolism*, (Kader, J. C., and Mazliak, P., eds), pp53–536, Kluwer Academic Publishers.
10 Bell and Cronan (1975), *J. Biol. Chem.* 250, 7147–7152.
11 Datla R S, Hammerlindl J K, Panchuk B, Pelcher L E, Keller W. (1992). *Modified binary plant transformation vectors with the wild-type gene encoding NPTII.; Gene* 122:383–384.
12 Frisch D A, Harris-Haller L W, Yokubaitis N T, Thomas T L, Hardin S H, Hall T C. (1995). *Complete sequence of the binary vector Bin19; Plant Mol Biol* 27:405–409.
13 Roesler K, Shintani D, Savage L, Boddupalli S, Ohlrogge J B (1997) *Targeting of the Arabidopsis homomeric acetyl-coenzyme A carboxylase to plastids of rapeseeds; Plant Physiol* 113: 75–81.
14 Meyerowitz, E. M. and Chang, C. (1985) Molecular biology of plant growth and development: *Arabidopsis thaliana* as an experimental system. In: Developmental Biology, Vol. 5, Plenum Press, NY., pp. 353–366.
15 Meyerowitz, E. M. (1987) *Arabidopsis thaliana*. Ann. Rev. Genet. 21: 93–111.
16 Goodman, H. M., Ecker, J. R. and Dean, C. (1995) The genome of *Arabidopsis thaliana*. Proc. Nat'l. Acad. Sci. USA 92: 10831–10835.
17 Lagercrantz, U., Putterill, J., Coupland, G. and Lydiate, D. (1996) Comparative mapping in *Arabidopsis* and *Brassica*, fine scale genome collinearity and congruence of genes controlling flowering. Plant J. 9: 13–20.
18 see for example: Zou et al., U.S. Pat. No: 6,051,755, Apr. 18, 2000.
19 Katavic et al. (1995), *Plant Physiol.* 108,399–409.
20 Bechtolds et al. (*CR. Acad. Sci. Paris, Sciences de la vie/Life sciences* 316, 1194–1199.
21 Katavic et al. (1995) *Plant Physiol.* 108:399–409.

22 Apse et al (1999) *Science* 285, 1256–1258.
23 Murashige and Skoog (1962), *Physiol Plant* 15: 473–497.
24 J. Biol. Chem. (1969), 244, 3316–3333.
25 Cronan and Bell; (1974), *J. Bacteriol.* 118, 598–605.
26 Ye and Larson (1988), *J. Bacteriol.*, 170, 4209–4215.
27 Bell and Cronan (1975), *J. Biol. Chem.* 250, 7147–7152.
28 Gardiner et al (1982), *Plant Physiol.* 70, 1316–1320.
29 Apse et al (1999) *Science* 285, 1256–1258.

---

What is claimed is:

1. A method for expressing in a plant a heterologous glycerol-3-phosphate dehydrogenase that is less sensitive to feedback inhibition than a wild-type glycerol-3-phosphate dehydrogenase of the plant, the method comprising the steps of:

provides a vector comprising a DNA sequence encoding a heterologous glycerol-3-phosphate dehydrogenase that is less sensitive to feedback inhibition than the wild-type glycerol-3-phosphate dehydrogenase of the plant; and transforming the plant with the vector, wherein the DNA sequence comprises a DNA sequence encoding the amino acid sequence listed in SEQ ID NO:2.

2. The method according to claim 1, wherein the DNA sequence comprises the nucleotide sequence listed in SEQ ID NO:1.

3. A method for expressing in a plant a heterologous glycerol-3-phosphate dehydrogenase that is less sensitive to feedback inhibition than a wild-type glycerol-3-phosphate dehydrogenase of the plant, the method comprising the steps of:

providing a vector comprising a DNA sequence encoding a heterologous glycerol-3-phosphate dehydrogenase that is less sensitive to feedback inhibition than the wild-type glycerol-3-phosphate dehydrogenase of the plant; and transforming the plant with the vector, wherein the heterologous glycerol-3-phosphate dehydrogenase has the amino acid sequence listed in SEQ ID NO:2.

4. A plant expressing a heterologous glycerol-3-phosphate dehydrogenase that is less sensitive to feedback inhibition than a wild-type glycerol-3-phosphate dehydrogenase of the plant, wherein the plant comprises a DNA sequence encoding the amino acid sequence listed in SEQ ID NO:2.

5. The plant according to claim 4, wherein the plant comprises a DNA sequence as listed in SEQ ID NO:1.

6. A plant expressing a heterologous glycerol-3-phosphate dehydrogenase that is less sensitive to feedback inhibition than a wild-type glycerol-3-phosphate dehydrogenase of the plant, wherein the heterologous glycerol-3-phosphate dehydrogenase has the amino acid sequence listed in SEQ ID NO:2.

7. A method for producing a genetically altered plant having altered fatty acid content in its glycerolipids, the method comprising the steps of:

providing a vector comprising a DNA sequence encoding a heterologous glycerol-3-phosphate dehydrogenase that is less sensitive to feedback inhibition than a wild-type glycerol-3-phosphate dehydrogenase of the plant; and transforming the plant with the vector, wherein the DNA sequence comprises a DNA sequence encoding the amino acid sequence listed in SEQ ID NO:2.

8. The method according to claim 7, wherein the DNA sequence comprises the nucleotide sequence listed in SEQ ID NO:1.

9. A method for producing a genetically altered plant having altered fatty acid content in its glycerolipids, the method comprising the steps of:

providing a vector comprising a DNA sequence encoding a heterologous glycerol-3-phosphate dehydrogenase that is less sensitive to feedback inhibition than a wild-type glycerol-3-phosphate dehydrogenase of the plant; and transforming the plant with the vector, wherein the heterologous glycerol-3-phosphate dehydrogenase has the amino acid sequence listed in SEQ ID NO:2.

10. A method for producing a genetically altered plant having increased stress tolerance relative to the wild-type levels of stress tolerance of the plant, the method comprising the steps of:

providing a vector comprising a DNA sequence encoding a heterologous glycerol-3-phosphate dehydrogenase that is less sensitive to feedback inhibition than a wild-type glycerol-3-phosphate dehydrogenase of the plant; and transforming the plant with the vector, wherein the DNA sequence comprises a DNA sequence encoding the amino acid sequence listed in SEQ ID NO:2.

11. The method according to claim 10, wherein the DNA sequence encoding the heterologous glycerol-3-phosphate dehydrogenase comprises the sequence listed in SEQ ID NO. 1.

12. A method for producing a genetically altered plant having increased stress tolerance relative to the wild-type levels of stress tolerance of the plant, the method comprising the steps of:

providing a vector comprising a DNA sequence encoding a heterologous glycerol-3-phosphate dehydrogenase that is less sensitive to feedback inhibition than a wild-type glycerol-3-phosphate dehydrogenase of the plant; and transforming the plant with the vector, wherein the heterologous glycerol-3-phosphate dehydrogenase has the amino acid sequence listed in SEQ ID NO:2.

13. A plant or plant progeny expressing a heterologous glycerol-3-phosphate dehydrogenase that is less sensitive to feedback inhibition than a wild-type glycerol-3-phosphate dehydrogenase of the plant, said plant comprising: the heterologous glycerol-3-phosphate dehydrogenase comprising a DNA sequence encoding the amino acid sequence of SEQ ID NO:2.

14. A transgenic plant or progeny thereof comprising: a DNA sequence encoding the amino acid sequence of SEQ ID NO:2.

* * * * *

SEQUENCE LISTING

<160> NUMBER OF SEQ ID NOS: 6

<210> SEQ ID NO 1
<211> LENGTH: 1020
<212> TYPE: DNA
<213> ORGANISM: Escherichia coli

<400> SEQUENCE: 1

```
atgaaccaac gtaatgcttc aatgactgtg atcggtgccg gctcgtacgg caccgctctt      60
gccatcaccc tggcaagaaa tggccacgag gttgtcctct ggggccatga ccctgaacat     120
atcgcaacgc ttgaacgcga ccgctgtaac gccgcgtttc tccccgatgt gccttttccc     180
gatacgctcc atcttgaaag cgatctcgcc actgcgctgg cagccagccg taatattctc     240
gtcgtcgtac ccagccatgt ctttggtgaa gtgctgcgcc agattaaacc actgatgcgt     300
cctgatgcgc gtctggtgtg ggcgaccaaa gggctggaag cggaaaccgg acgtctgtta     360
caggacgtgg cgcgtgaggc cttaggcgat caaattccgc tggcggttat ctctggccca     420
acgtttgcga aagaactggc ggcaggttta ccgacagcta tttcgctggc ctcgaccgat     480
cagacctttg ccgatgatct ccagcagctg ctgcactgcg gcaaaagttt ccgcgtttac     540
agcaatccgg atttcattgg cgtgcagctt ggcggcgcgg tgaaaaacgt tattgccatt     600
ggtgcgggga tgtccgacgg tatcggtttt ggtgcgaatg cgcgtacggc gctgatcacc     660
cgtgggctgg ctgaaatgtc gcgtcttggt gcggcgctgg gtgccgaccc tgccaccttt     720
atgggcatgg cggggcttgg cgatctggtg cttacctgta ccgaaaacca gtcgcgtaac     780
cgccgttttg gcatgatgct cggtcagggc atggatgtac aaagcgcgca ggagaagatt     840
ggtcaggtgg tggaaggcta ccgcaatacg aaagaagtcc gcgaactggc gcatcgcttc     900
ggcgttgaaa tgccaataac cgaggaaatt tatcaagtat tatattgcgg aaaaaacgcg     960
cgcgaggcag cattgacttt actaggtcgt gcacgcaagg acgagcgcag cagccactaa    1020
```

<210> SEQ ID NO 2
<211> LENGTH: 339
<212> TYPE: PRT
<213> ORGANISM: Escherichia coli

<400> SEQUENCE: 2

Met Asn Gln Arg Asn Ala Ser Met Thr Val Ile Gly Ala Gly Ser Tyr
 1               5                  10                  15

Gly Thr Ala Leu Ala Ile Thr Leu Ala Arg Asn Gly His Glu Val Val
            20                  25                  30

Leu Trp Gly His Asp Pro Glu His Ile Ala Thr Leu Glu Arg Asp Arg
        35                  40                  45

Cys Asn Ala Ala Phe Leu Pro Asp Val Pro Phe Pro Asp Thr Leu His
    50                  55                  60

Leu Glu Ser Asp Leu Ala Thr Ala Leu Ala Ala Ser Arg Asn Ile Leu
65                  70                  75                  80

Val Val Val Pro Ser His Val Phe Gly Glu Val Leu Arg Gln Ile Lys
                85                  90                  95

Pro Leu Met Arg Pro Asp Ala Arg Leu Val Trp Ala Thr Lys Gly Leu

-continued

```
                        100                 105                 110
Glu Ala Glu Thr Gly Arg Leu Leu Gln Asp Val Ala Arg Glu Ala Leu
            115                 120                 125
Gly Asp Gln Ile Pro Leu Ala Val Ile Ser Gly Pro Thr Phe Ala Lys
130                 135                 140
Glu Leu Ala Ala Gly Leu Pro Thr Ala Ile Ser Leu Ala Ser Thr Asp
145                 150                 155                 160
Gln Thr Phe Ala Asp Asp Leu Gln Gln Leu Leu His Cys Gly Lys Ser
                165                 170                 175
Phe Arg Val Tyr Ser Asn Pro Asp Phe Ile Gly Val Gln Leu Gly Gly
                180                 185                 190
Ala Val Lys Asn Val Ile Ala Ile Gly Ala Gly Met Ser Asp Gly Ile
                195                 200                 205
Gly Phe Gly Ala Asn Ala Arg Thr Ala Leu Ile Thr Arg Gly Leu Ala
210                 215                 220
Glu Met Ser Arg Leu Gly Ala Ala Leu Gly Ala Asp Pro Ala Thr Phe
225                 230                 235                 240
Met Gly Met Ala Gly Leu Gly Asp Leu Val Leu Thr Cys Thr Glu Asn
                245                 250                 255
Gln Ser Arg Asn Arg Arg Phe Gly Met Met Leu Gly Gln Gly Met Asp
                260                 265                 270
Val Gln Ser Ala Gln Glu Lys Ile Gly Gln Val Val Glu Gly Tyr Arg
                275                 280                 285
Asn Thr Lys Glu Val Arg Glu Leu Ala His Arg Phe Gly Val Glu Met
                290                 295                 300
Pro Ile Thr Glu Glu Ile Tyr Gln Val Leu Tyr Cys Gly Lys Asn Ala
305                 310                 315                 320
Arg Glu Ala Ala Leu Thr Leu Leu Gly Arg Ala Arg Lys Asp Glu Arg
                    325                 330                 335
Ser Ser His

<210> SEQ ID NO 3
<211> LENGTH: 18
<212> TYPE: DNA
<213> ORGANISM: Artificial Sequence
<220> FEATURE:
<223> OTHER INFORMATION: Description of Artificial Sequence:PCR primer
      GPSA3

<400> SEQUENCE: 3
ttagtggctg ctgcgctc                                                    18

<210> SEQ ID NO 4
<211> LENGTH: 18
<212> TYPE: DNA
<213> ORGANISM: Artificial Sequence
<220> FEATURE:
<223> OTHER INFORMATION: Description of Artificial Sequence:PCR primer
      GPSA5

<400> SEQUENCE: 4
aacaatgaac caacgtaa                                                    18

<210> SEQ ID NO 5
<211> LENGTH: 26
<212> TYPE: DNA
<213> ORGANISM: Artificial Sequence
<220> FEATURE:
<223> OTHER INFORMATION: Description of Artificial Sequence:PCR pimer
```

-continued

```
          GPSA31

<400> SEQUENCE: 5
gagagctctt agtggctgct gcgctc                                          26

<210> SEQ ID NO 6
<211> LENGTH: 30
<212> TYPE: DNA
<213> ORGANISM: Artificial Sequence
<220> FEATURE:
<223> OTHER INFORMATION: Description of Artificial Sequence:PCR primer
      GPSA51

<400> SEQUENCE: 6
gaagaaggat ccaacaatga accaacgtaa                                      30
```